(12) United States Patent
Wong et al.

(10) Patent No.: US 11,074,802 B2
(45) Date of Patent: Jul. 27, 2021

(54) METHOD AND APPARATUS FOR AUTOMATIC EVENT PREDICTION

(71) Applicant: Hill-Rom Services, Inc., Batesville, IN (US)

(72) Inventors: Alexander Sheung Lai Wong, Waterloo (CA); Yongji Fu, Harrison, OH (US); Brendan James Chwyl, Waterloo (CA); Audrey Gina Chung, Waterloo (CA); Mohammad Javad Shafiee, Kitchener (CA)

(73) Assignee: Hill-Rom Services, Inc., Batesville, IN (US)

( * ) Notice: Subject to any disclaimer, the term of this patent is extended or adjusted under 35 U.S.C. 154(b) by 631 days.

(21) Appl. No.: 15/883,754

(22) Filed: Jan. 30, 2018

(65) Prior Publication Data

US 2018/0218587 A1 Aug. 2, 2018

Related U.S. Application Data

(60) Provisional application No. 62/453,857, filed on Feb. 2, 2017.

(51) Int. Cl.
| | |
|---|---|
| *G08B 21/22* | (2006.01) |
| *G06K 9/00* | (2006.01) |
| *G06N 3/04* | (2006.01) |
| *G06K 9/66* | (2006.01) |
| *G06K 9/62* | (2006.01) |
| *A61B 5/11* | (2006.01) |

(Continued)

(52) U.S. Cl.
CPC ............ *G08B 21/22* (2013.01); *A61B 5/0077* (2013.01); *A61B 5/1115* (2013.01); *A61B 5/7267* (2013.01); *G06K 9/00342* (2013.01); *G06K 9/00771* (2013.01); *G06K 9/4628* (2013.01); *G06K 9/6273* (2013.01); *G06K 9/6277* (2013.01); *G06K 9/66* (2013.01); *G06N 3/0472* (2013.01)

(58) Field of Classification Search
None
See application file for complete search history.

(56) References Cited

U.S. PATENT DOCUMENTS

| | | |
|---|---|---|
| 4,539,560 A | 9/1985 | Fleck et al. |
| 4,803,744 A | 2/1989 | Peck et al. |

(Continued)

OTHER PUBLICATIONS

Shou Z, Wang D, Chang SF. Temporal action localization in untrimmed videos via multi-stage cnns. InProceedings of the IEEE Conference on Computer Vision and Pattern Recognition 2016 (pp. 1049-1058). (Year: 2016).*

(Continued)

*Primary Examiner* — David Perlman
(74) *Attorney, Agent, or Firm* — Barnes & Thornburg LLP

(57) ABSTRACT

A method and apparatus for predicting hospital bed exit events from video camera systems is disclosed. The system processes video data with a deep convolutional neural network consisting of five main layers: a 1×1 3D convolutional layer used for generating feature maps from raw video data, a context-aware pooling layer used for rectifying data from different camera angles, two fully connected layers used for applying pre-trained deep features, and an output layer used to provide a likelihood of a bed exit event.

24 Claims, 6 Drawing Sheets

(51) Int. Cl.
*G06K 9/46* (2006.01)
*A61B 5/00* (2006.01)

(56) References Cited

U.S. PATENT DOCUMENTS

| | | | |
|---|---|---|---|
| 4,934,468 A | | 6/1990 | Koerber, Sr. et al. |
| 4,953,244 A | | 9/1990 | Koerber, Sr. et al. |
| 5,276,432 A | | 1/1994 | Travis |
| 6,049,281 A | * | 4/2000 | Osterweil ............ A61B 5/1128 340/573.1 |
| 6,067,019 A | | 5/2000 | Scott |
| 7,020,335 B1 | * | 3/2006 | Abousleman ........ G06K 9/3241 375/240.11 |
| 9,373,059 B1 | * | 6/2016 | Heifets ................ G06K 9/4628 |
| 2016/0063846 A1 | | 3/2016 | Lemire et al. |
| 2016/0239725 A1 | * | 8/2016 | Liu ......................... G06T 5/002 |
| 2017/0007187 A1 | * | 1/2017 | Breneisen ............ A61B 5/0075 |

OTHER PUBLICATIONS

Extended European Search Report in related EP3358498B1, dated Jun. 28, 2018, 10 pages.

Martinez M., Schauerte B., Stiefelhagen R. (2013) "BAM!" Depth-Based Body Analysis in Critical Care. In: Wilson R., Hancock E., Bors A., Smith W. (eds) Computer Analysis of Images and Patterns. CAIP 2013. Lecture Notes in Computer Science, vol. 8047. Springer, Berlin, Heidelberg. https://doi.org/10.1007/978-3-642-40261-6_56.

B. Chwyl, A. G. Chung, M. J. Shafiee, Y. Fu and A. Wong, "DeepPredict: A deep predictive intelligence platform for patient monitoring," 2017 39th Annual International Conference of the IEEE Engineering in Medicine and Biology Society (EMBC), Seogwipo, 2017, pp. 4309-4312, doi: 10.1109/EMBC.2017. 8037809.

Achilles F., Ichim AE., Coskun H., Tombari F., Noachtar S., Navab N. (2016) Patient MoCap: Human Pose Estimation Under Blanket Occlusion for Hospital Monitoring Applications. In: Ourselin S., Joskowicz L., Sabuncu M., Unal G., Wells W. (eds) Medical Image Computing and Computer-Assisted Intervention—MICCAI 2016. MICCAI 2016. Lecture Notes in Computer Science, vol. 9900. Springer, Cham. https://doi.org/10.1007/978-3-319-46720-7_57.

Grimm, Timo & Martinez, Manuel & Benz, Andreas & Stiefelhagen, Rainer. (2016). Sleep position classification from a depth camera using Bed Aligned Maps. 319-324. 10.1109/ICPR.2016.7899653.

Office Action in related JP6724051B2, dated Jul. 3, 2019, 2 pgs.

* cited by examiner

METHOD AND APPARATUS FOR AUTOMATIC EVENT PREDICTION

PRIORITY CLAIM

This application claims priority under 35 U.S.C. § 119(e) to U.S. Provisional Application No. 62/453,857, filed Feb. 2, 2017, which is expressly incorporated by reference herein.

BACKGROUND

The present disclosure is related to the use of cameras in a patient environment to collect image data and predict adverse events. More specifically, the present disclosure is related to a method of establishing a likelihood of a bed exit event using real time image data that is modified by pre-trained deep features using a neural network.

A prominent concern in healthcare facilities is the limited number of available healthcare providers (e.g., nurses, doctors) relative to the growing number of patients. One area that can be automated to potentially improve the overall work flow is the monitoring of patient's bed exit events from hospital beds. Automatic bed exit detection systems have previously been proposed to assist healthcare providers.

U.S. Pat. No. 5,276,432 discloses a system which uses four load cells to measure weight at each corner of a hospital bed. The patient's center of gravity with respect to the bed frame is calculated using the information captured by the load cells. If the center of gravity of the patient is not contained within a predetermined region, a bed exit event is said to be detected. Similarly, Scott [9] has patented a system in which the presence of a patient is detected by a multitude of sensors. Specifically, the presence or absence of a patient is determined by the dielectric constant, which is measured within a predefined detection space.

U.S. Published Patent Application No. 20160063846 discloses a system which, in addition to detecting the presence of a patient, aims to determine the location of a patient on a hospital bed. The proposed system uses a patient support assembly on a frame which consists of at least one deformation sensor, indicating the deformation of the frame. A location determination unit is connected to the deformation sensor to provide the lateral or longitudinal location of the patient, depending on the deformation sensor's location.

While methods exist for detecting bed exit events, detecting these exit events as they occur does not allow for a healthcare professional to provide timely assistance during the exit event. A system for automatic bed exit prediction would enable the notification of healthcare providers prior to a bed exit event so that prompt assistance can be provided to patients. This would significantly lower the potential for patient injuries (e.g., falls, strains) occurring during an unassisted bed exit event.

SUMMARY

The present application discloses one or more of the features recited in the appended claims and/or the following features which, alone or in any combination, may comprise patentable subject matter:

According to a first aspect of the present disclosure, an apparatus for predicting that a patient is about to exit from a patient support apparatus comprises a camera positioned with the patient support apparatus in the field of view of the camera and a controller receiving signals representative of images from the camera. The controller is operable to capture time sequenced video images from the camera. The controller is also operable to input the time sequenced video images to a convolution layer and the time sequenced video images are convolved with a convolution kernel to produce a defined number of feature maps. The controller is further operable to input the feature maps into a context-aware pooling layer to extract relevant features of interest from the feature maps and generate feature vectors. The controller is still further operable to input a feature vector to a first fully connected layer such that each element of the feature vector is connected to a plurality of artificial neurons in the first fully connected layer and each combination outputs a first connected layer value. The controller is yet still further operable to input the values derived by each combination of first fully connected layer into a second fully connected layer such that each value is connected to a plurality of artificial neurons in the second fully connected layer such that each combination outputs a second connected layer value. The controller is yet still further operable to input the second connected layer values into an output layer which provides a non-exit probability which defines the likelihood that a patient exit event will not occur in a predetermined time and an exit probability which defines the likelihood that a patient exit event will occur in the predetermined time. The controller is yet still also operable to utilize the non-exit probability and exit probability to determine the likelihood of a patient exit event to generate a signal when the determine likelihood of a patient exit event exceeds a threshold value. The controller is also operable, if the signal is generated based on the determined likelihood of a patient exit event exceeds a threshold value, to generate a notification of the impending event.

In some embodiments of the first aspect, the convolution layer applies a rectifier when the feature maps are generated.

In some embodiments of the first aspect, the rectifier introduces non-saturating linearity to the features maps.

In some embodiments of the first aspect, the rectifier is an absolute value function.

In some embodiments of the first aspect, the context-aware pooling layer rectifies for a variation in the camera's field of view.

In some embodiments of the first aspect, the first fully connected layer includes 50 artificial neurons.

In some embodiments of the first aspect, the second fully connected layer comprises 10 artificial neurons.

In some embodiments of the first aspect, the first fully connected layer and second fully connected layer apply a transfer function.

In some embodiments of the first aspect, the transfer function is the tansig(x) function.

In some embodiments of the first aspect, the first fully connected layer and the second fully connected layer are developed by training via stochastic gradient descent to produce a set of deep features.

According to a second aspect of the present disclosure, a method of predicting that a patient is about to exit from a patient support apparatus that is in the field of view of a camera comprises receiving signals representative of images from the camera and capturing time sequenced video images from the camera. The method also comprises inputting the time sequenced video images to a convolution layer and convolving the time sequenced video images with a convolution kernel to produce a defined number of feature maps. The method further comprises inputting the feature maps into a context-aware pooling layer to extract relevant features of interest from the feature maps and generate feature vectors. The method still also comprises inputting a feature vector to a first fully connected layer such that each element of the feature vector is connected to a plurality of artificial neurons in the first fully connected layer and each combination outputs a first connected layer value. The method still further comprises inputting the values derived by each combination of first fully connected layer into a second fully connected layer such that each value is connected to a plurality of artificial neurons in the second fully connected layer such that each combination outputs a second connected layer value. The method yet still further comprises inputting the second connected layer values into an output layer which provides a non-exit probability which defines the likelihood that a patient exit event will not occur in a predetermined time and an exit probability which defines the likelihood that a patient exit event will occur in the predetermined time. The method also further comprises utilizing the non-exit probability and exit probability to determine the likelihood of a patient exit event to generate a signal when the determined likelihood of a patient exit event exceeds a threshold value. The method also still further comprises, if the signal is generated based on the determined likelihood of a patient exit event exceeds a threshold value, generating a notification of the impending event.

In some embodiments of the second aspect, the convolution layer applies a rectifier when the feature maps are generated.

In some embodiments of the second aspect, the rectifier introduces non-saturating linearity to the features maps.

In some embodiments of the second aspect, the rectifier is an absolute value function.

In some embodiments of the second aspect, the context-aware pooling layer rectifies for a variation in the camera's field of view.

In some embodiments of the second aspect, the first fully connected layer includes 50 artificial neurons.

In some embodiments of the second aspect, the second fully connected layer comprises 10 artificial neurons.

In some embodiments of the second aspect, the first fully connected layer and second fully connected layer apply a transfer function.

In some embodiments of the second aspect, the transfer function is the tansig(x) function.

In some embodiments of the second aspect, the first fully connected layer and the second fully connected layer are developed by training via stochastic gradient descent to produce a set of deep features.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
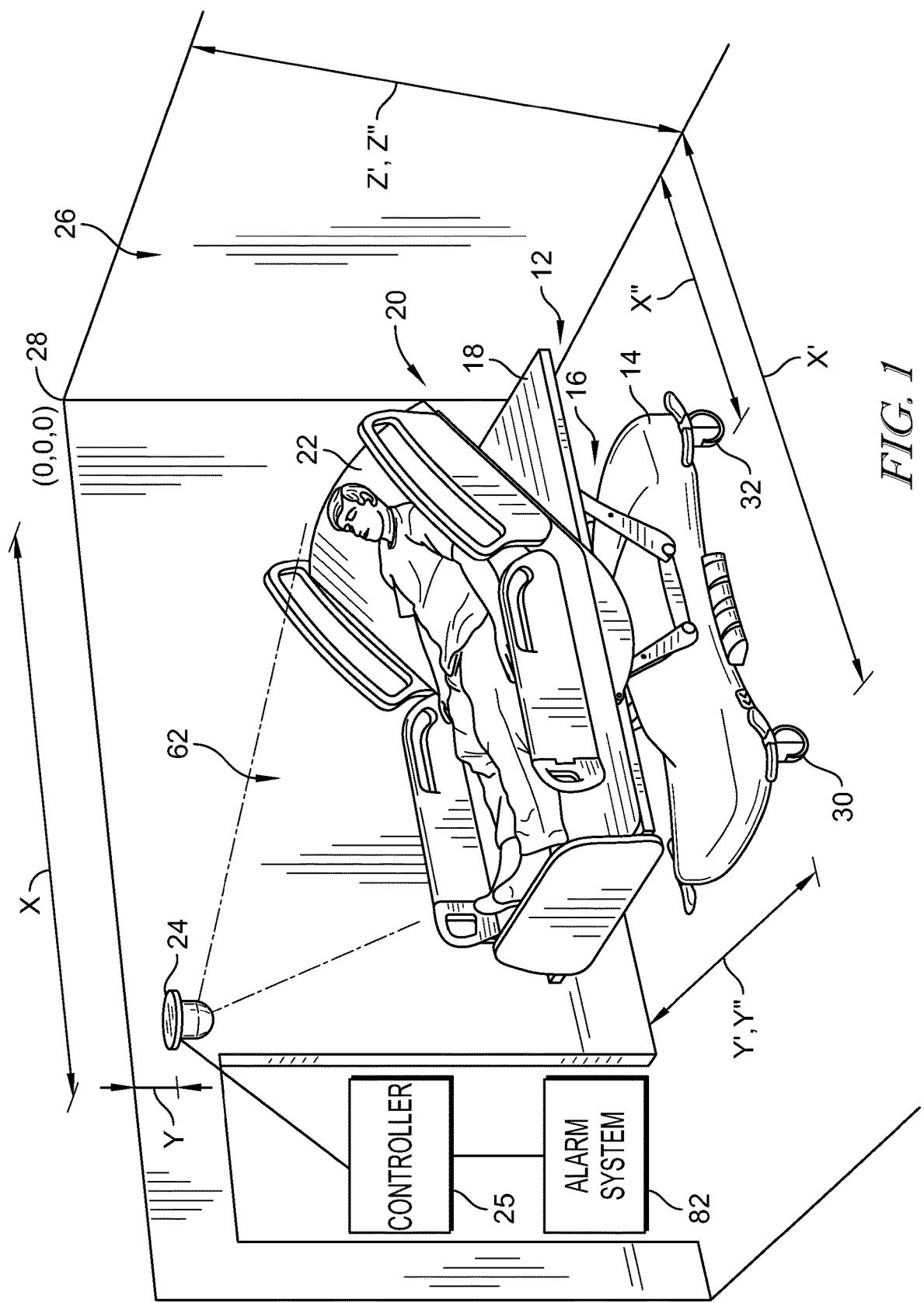
FIG. 1 is a perspective view of a camera mounted in a room and a patient support apparatus positioned in a field of view of the camera.

Referring to FIG. 1, a patient 10 is shown to be positioned on a patient support apparatus 12, illustratively embodied as a hospital bed. In other embodiments, the patient support apparatus may be embodied as a chair, a wheelchair, a table, a gurney, a stretcher, or the like. The hospital bed 12 has a base 14, a lift system 16, an upper frame 18, and a deck 20 with at least one articulated deck section 22. The articulated deck section 22 is movable relative to the upper frame 18 to a plurality of positions. A camera 24 is positioned on a ceiling (not shown) of a room 26 in a fixed location having coordinates X, Y, Z relative to an origin or datum 28 of the room 26. The camera 24 is connected to a controller 25 which receives signals form the camera 24 indicative of the images captured by the camera 24. The controller 25 is operable to perform use the signal to establish the likelihood that a patient will exit the patient support apparatus in a predetermined time period, as will be discussed in further detail below. If such a signal is generated, the signal is acted upon by an alarm system 82 to provide either an electronic record of the alarm condition, an auditory alarm, or a visual alarm, or any combination of the three.

The relative location of the bed 12 is established by identifying the position of two components of the bed 12. For example, the location of a first caster 30 is defined by coordinates X', Y', Z' and the location of a second caster 32 is defined by coordinates X", Y", Z". The relative position of the bed 10 to the camera 24 is used by an algorithm to rectify the position of the bed 10 in predicting bed exits from the video data from the camera 24. The presently disclosed analysis platform is a deep convolutional neural network trained to predict patient exits from the bed 10 from video data.

Figure 2:
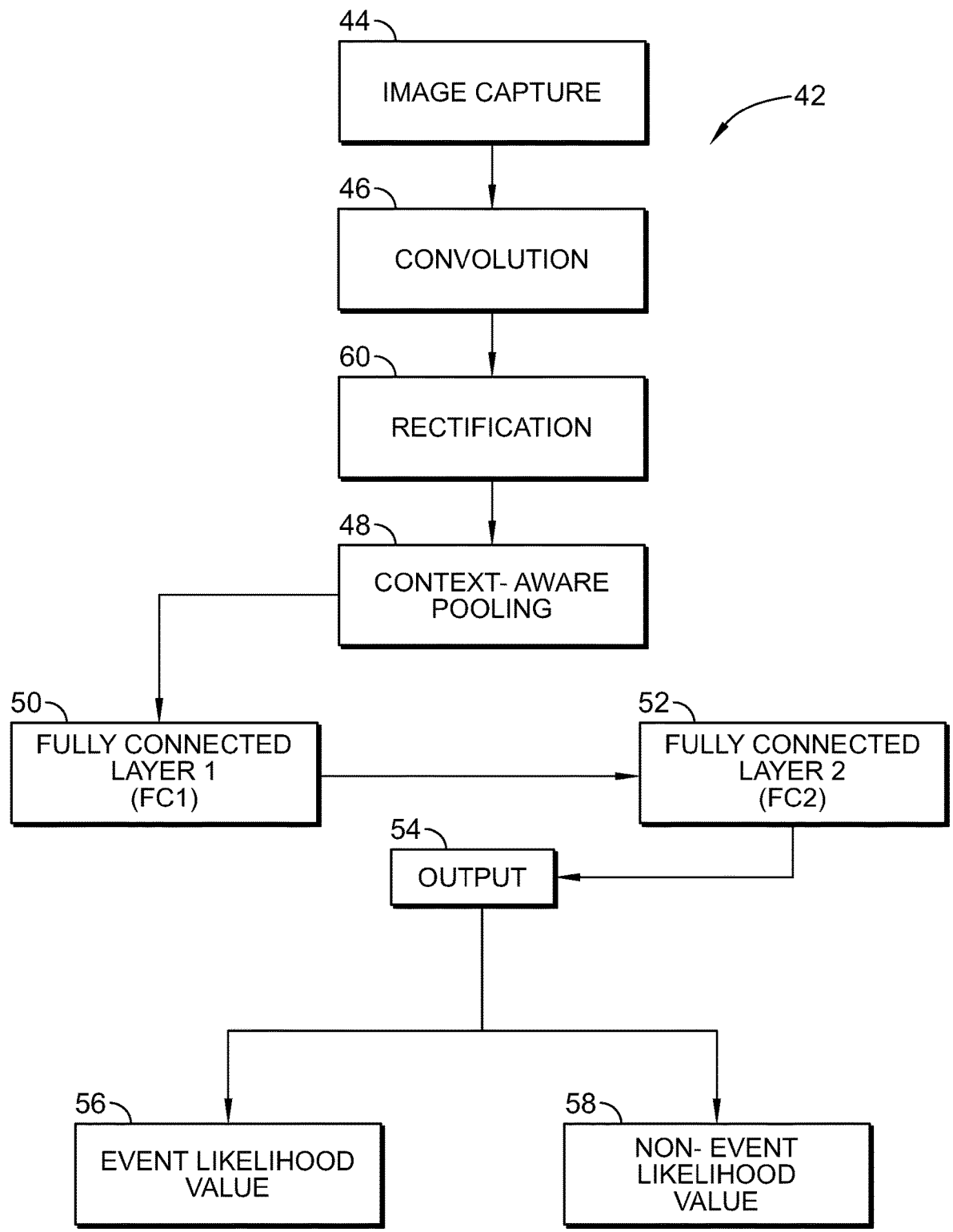
FIG. 2 is a process flow chart for a controller to monitor images from the camera and predict, based on information derived from the images, that a patient is likely to exit the bed in some predetermined future time interval.

To achieve consistent temporal resolution from a wide variety of video data, all video sequences are subsampled to a frame rate of one frame per second. It should be understood that while a frame rate of one frame per second is used in the illustrative embodiment, other frame rates may be used. Referring to the process 42 shown in FIG. 2 which applies a model shown in FIG. 3, windowed sequences of video image frames 34 are captured at a step 44 and first processed by a 1×1 3D convolutional layer 36 at step 46 to extract feature maps. In some embodiments, the feature maps are rectified as suggested by optional step 60. These feature maps are then subjected to a context-aware pooling layer 38 at step 48 where meaningful feature vectors are extracted from each feature map, independent of the video camera's view point. At step 50, the feature map is processed at a first fully connected layer (FC1). The output of the first fully connected layer is then processed by a second fully connected layer (FC2) at step 52. The two fully connected layers FC1 and FC2 impose non-linearity into the extracted feature set. These values proceed to an output layer 40 analysis at step 54 with two values being output: one corresponding to the likelihood of a bed exit event occurring in the near future 56, and the other corresponding to the likelihood of a bed exit event not occurring in the near future 58.

The 1×1 3D convolutional layer 36 is applied at step 44 to the windowed sequence of image frames 34, defined as an n×m×(3×N) matrix where n and m correspond to the width and height of each frame, N corresponds to the number of frames contained in the windowed sequence, and 3 represents the number of color channels for each image. Convolution in image processing is the process of adding each element of the image to its local neighbors, weighted by a kernel. A kernel is a signal processing value, generalized as a matrix, with the kernel being developed based on empirical data. For example, in a particular case where two three-by-three matrices, one a kernel, and the other an image piece, is convolved by flipping both the rows and columns of the kernel and then multiplying locationally similar image values and summing the products. The [2,2] element of the resulting image would be a weighted combination of all the entries of the image matrix, with weights given by the kernel:

$$\left( \begin{bmatrix} a & b & c \\ d & e & f \\ g & h & i \end{bmatrix} * \begin{bmatrix} 1 & 2 & 3 \\ 4 & 5 & 6 \\ 7 & 8 & 9 \end{bmatrix} \right)[2,2] = (i*1) + (h*2) +$$

$$(g*3) + (f*4) + (e*5) + (d*6) + (c*7) + (b*8) + (a*9).$$

The other entries would be similarly weighted, where the kernel is positioned on the center of each of the boundary points of the image, and the weighted values are summed.

In the present disclosure, the windowed sequence image frame 34 matrix is inputted into the 3D convolutional layer 36, where a 1×1×(N×3) 3D convolutional kernel is convolved with each set of windowed video frames 34 to produce a set of N feature maps. This kernel is convolved along the first two dimensions (xy-plane) per pixel and convolved along the third dimension with a temporal stride of 3 to account for the three color channels of each frame. Again, the kernel is determined empirically.

At step 60 of the process 42, an absolute value rectifier is applied to introduce non-saturating nonlinearity to the layer. It should be understood that other functions may be applied to rectify the convolution layer in other embodiments and that the absolute value rectification is but one example of a function that drives non-saturating nonlinearity to the output from the convolution layer 36.

To achieve context-aware pooling, meaningful feature vectors must be extracted from the feature maps produced in the previous layer to accurately predict a bed exit event. The feature maps contain information from the video camera's entire field of view 62 (See FIG. 1); however, to rectify data collected from cameras with different fields of view, only the region of interest (i.e., the hospital bed) is considered. Context-aware pooling is used to extract relevant features from the region of interest.

Figure 3:
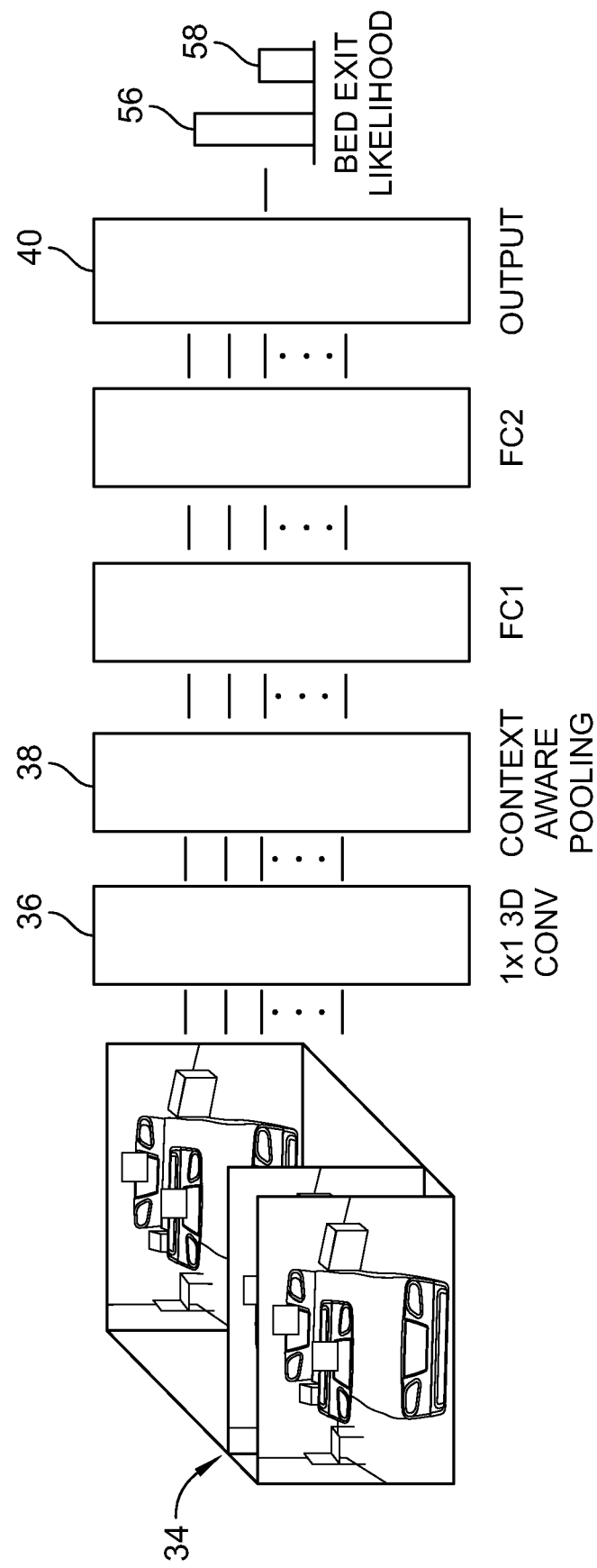
FIG. 3 is a model of the prediction system presently disclosed.
Figure 4:
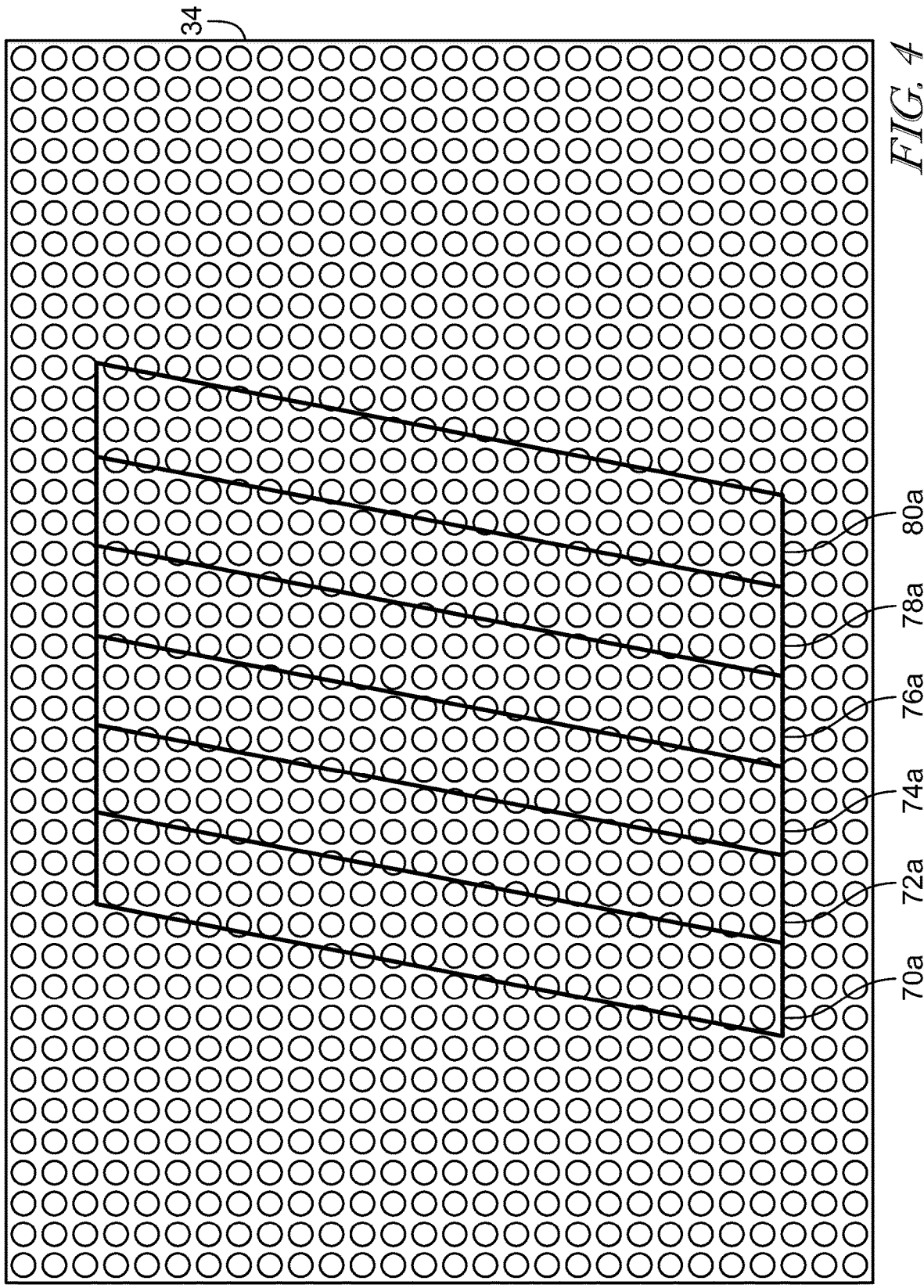
FIG. 4 is an illustration of a first segmentation approach used to segment video data when the patient support apparatus is arranged in a first configuration.

To determine the region of interest, a model of the hospital bed consisting of six regions 70a, 72a, 74a, 76a, 78a, and 80a is constructed as suggested in FIG. 4. The hospital bed 10 remains stationary relative to the video camera 24 throughout the duration of a video sequence, and a model of the hospital bed is built only once per video sequence. To facilitate context-aware pooling, each feature map is considered as a lattice of nodes where each node, x, represents a single feature within the map. For each feature map, nodes within each region, generalized as h, are subject to pooling and then concatenated to create a 1×(j×N) feature vector as shown in FIGS. 3 and 4. This is expressed mathematically as $$y = \text{pool}(x_i | i \in 2h_j) \text{ for all } j; \quad (1)$$

where $x_i$ represents the $i^{th}$ node in the region $h_j$, j is in the range [1, 6], and pool(.) is the pooling function. It should be understood that additional granularity may be developed by increasing the number of regions from 6 to some larger value.

Figure 5:
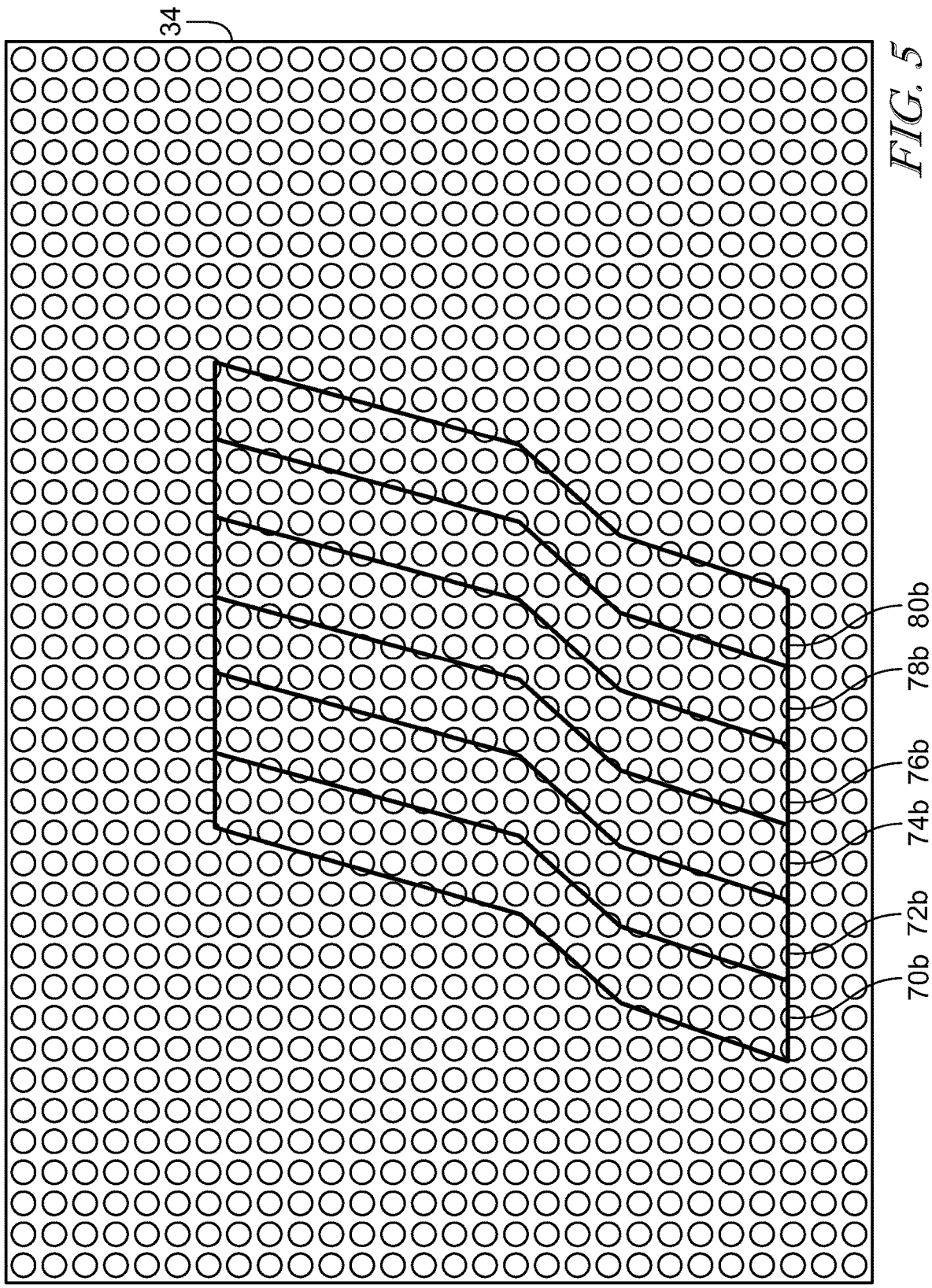
FIG. 5 is an illustration of a first segmentation approach used to segment video data when the patient support apparatus is arranged in a second configuration.

In situations where the position or orientation of the hospital bed 10 is in a different relationship to the camera 24 or if the bed 10 is in a different configuration, a different arrangement of six regions, 70b, 72b, 74b, 76b, 78b, and 80b may be applied to create the feature vector as suggested in FIG. 5. Using this approach, a rectification factor may be applied to correct for the differences between the developed kernel and the appropriate kernel to apply in a particular application.

Two fully connected layers, FC1 and FC2, exist in this platform to provide non-linearity. Each element of the feature vector is connected to each of the 50 artificial neurons contained in FC1. In turn, each artificial neuron in FC1 is connected to each of the 10 artificial neurons contained in FC2, which are then connected to the output layer. These layers are trained via stochastic gradient descent in order to produce a set of deep features that enable prediction of whether a patient exit event will occur in the near future. Both fully connected layers use the tansig transfer function, defined as:

$$\text{tansig}(x) = \frac{2}{1 + \exp(-2x)} - 1 \quad (2)$$

The output layer employs soft-max pooling and provides an interpretable likelihood of a bed exit event, with one artificial neuron representing the likelihood of a bed exit event occurring and the other artificial neuron representing the likelihood that a bed exit event will not occur. The likelihood is provided as a decimal value ranging from 0 to 1, where 0 suggests that a bed exit event is very unlikely and 1 suggests that a bed exit event is very likely.

Example

To verify the efficacy of the system, a dataset consisting of 187 hours of 3 channel red-green-blue (RGB) video data was used. The dataset was segmented into 1009 windowed sequences of data, each 40 seconds in length. These windows were manually selected such that, for positive samples, a bed exit event occurred at 30 seconds, while no bed exit event occurred within the windowed sequence for negative samples.

A correct positive prediction was said to have occurred if the predicted likelihood of a bed exit event exceeded a confidence threshold, τ, at any point in the seven seconds preceding the bed exit event whereas a correct negative prediction was said to have occurred if the predicted likelihood of a bed exit event remained below τ in the same time interval. The number of frames per window, N, was set to 7. The pooling function in the context-aware pooling layer was defined as the average of all nodes within a given region.

Using the segmented dataset, two experiments were run. First, the value of τ was altered to determine its optimal value with respect to accuracy. Second, the platform's fully connected layers were trained using different amounts of data to observe its effect on accuracy, sensitivity, and specificity.

Figure 6:
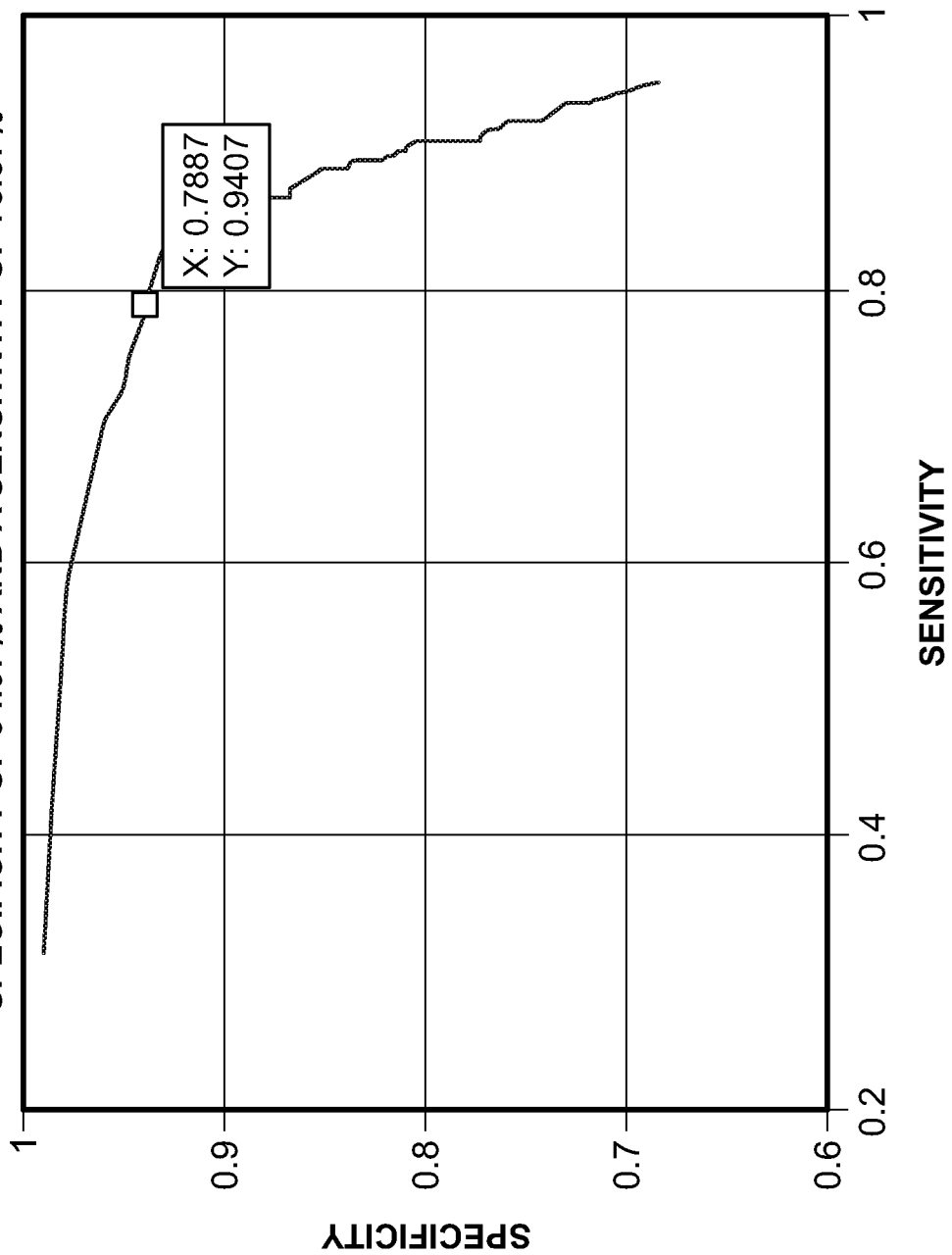
FIG. 6 is a plot of the relationship of specificity to sensitivity for a particular dataset analyzed by the prediction system of the present disclosure.

While a maximum accuracy of 90% was determined to occur when τ=0.89, it is important to consider the sensitivity and specificity values in the context of the application. In the case of bed exit prediction, it is preferable to decrease τ in order to increase sensitivity, thereby missing fewer bed exit events. However, there is a sensitivity-specificity tradeoff, and this results in decreased specificity. FIG. 6 shows the relationship between specificity and sensitivity as τ is varied from 0 to 1. A value of τ=0.73 was empirically determined to provide a good balance between specificity and sensitivity for the application of bed exit prediction.

Using an empirically determined τ of 0.73, the values of accuracy, sensitivity, and specificity for three different platforms are tabulated in Table I. The platforms vary only in their fully connected layer, where each platform was trained using a different amount of data. Sensitivity decreases before slightly increasing and the specificity is initially improved before slightly dropping. Sensitivity and specificity are dependent on the number of positive and negative samples and their fluctuation is attributed to a varying ratio of positive and negative samples as the amount of training data was increased. Accuracy takes into account both positive and negative samples, and its steady increase indicates that the platform generally performs better when trained on more data.

TABLE I

A confidence interval of τ = 0.73 was used for these experiments.

| Hours of Data | Accuracy (%) | Sensitivity (%) | Specificity (%) |
|---|---|---|---|
| 180 | 86.47 | 78.87 | 94.07 |
| 140 | 85.13 | 74.65 | 95.60 |
| 19 | 83.54 | 81.18 | 85.89 |

Using the model trained on 180 hours of data, a confidence threshold of τ=0.73, and the entire unsegmented dataset, the average prediction time and relative between-error intervals were calculated (as shown in Table II). It can be seen that with this threshold, missed bed exit events are expected to occur only once every 3.1 hours while false alarms are expected to occur only once every 11 hours. The missed bed exit interval is thought to be lower than the expected false alarm interval due to the high proportion of negative samples to positive samples within this dataset.

It is noted that many of the false positives can be attributed to motion within the bed area. This was most commonly caused by participants moving a tray table or laptop computers on a tray table positioned over top of the bed and patient, but was also sometimes caused by moving shadows. Because all videos were subsampled to a frame rate of one frame per second, false negatives are likely due to rapid bed exits. In this case, the frame rate may be insufficient to capture the bed exit event in detail.

TABLE II

Mean prediction time and predicted time-between error intervals for the platform when trained on 180 hours of data and a confidence threshold of τ = 0.73

| Mean Prediction Time (s) | Expected Missed Bed Exit Interval | Expected False Alarm Interval |
|---|---|---|
| 10.96 ± 9.01 | 3.1 hours | 11 hours |

Results indicate that the approach is capable of predicting patient bed exit events of up to seven seconds in advance with a high degree of accuracy. It is contemplated that other embodiments may include automating the manual point selection process for generating the hospital bed model in the context-aware pooling layer to enable a completely automated system, as well as adding the capability for the system to automatically adapt in the event the hospital bed moves in relation to the camera view point. In addition, the platform can be further improved by incorporating data from any pre-existing bed sensors into the deep convolutional neural network architecture.

The following text is a draft paper titled "DeepPredict: A Deep Predictive Intelligence Platform for Patient Monitoring" which names the inventors of the present application as authors. The text forms part of the disclosure of this patent application. The draft paper is hereby incorporated into this provisional patent application by reference herein for all this it discloses regarding a system for predicting an impending patient exit from a patient support apparatus.

Although certain illustrative embodiments have been described in detail above, variations and modifications exist within the scope and spirit of this disclosure as described and as defined in the following claims.

The invention claimed is:

1. An apparatus for predicting that a patient is about to exit from a patient support apparatus, the apparatus comprising
a camera positioned with the patient support apparatus in the field of view of the camera,
a controller receiving signals representative of images from the camera, the controller operable to:
capture time sequenced video images from the camera,
input the time sequenced video images to a convolution layer and convolving the time sequenced video images with a convolution kernel to produce a defined number of feature maps,
input the feature maps into a context-aware pooling layer to extract relevant features of interest from the feature maps and generate feature vectors, wherein the context-aware pooling layer applies a rectification factor to the feature of interest to correct for the differences between the developed kernel and the appropriate kernel to be applied to account for a difference in the relationship of the position and orientation of the bed in the developed kernel and the actual position and orientation of the patient support apparatus,
input a feature vector to a first fully connected layer such that each element of the feature vector is connected to a plurality of artificial neurons in the first fully connected layer and each combination outputs a first connected layer value,
input the values derived by each combination of first fully connected layer into a second fully connected layer such that each value is connected to a plurality of artificial neurons in the second fully connected layer such that each combination outputs a second connected layer value, input the second connected layer values into an output layer which provides a non-exit probability which defines the likelihood that a patient exit event will not occur in a predetermined time and an exit probability which defines the likelihood that a patient exit event will occur in the predetermined time, utilize the non-exit probability and exit probability to determine the likelihood of a patient exit event to generate a signal when the determine likelihood of a patient exit event exceeds a threshold value, and if the signal is generated based on the determined likelihood of a patient exit event exceeds a threshold value, generating a notification of the impending event.

2. The apparatus of claim 1, wherein the convolution layer applies a rectifier when the feature maps are generated.

3. The apparatus of claim 2, wherein the rectifier introduces non-saturating linearity to the features maps.

4. The apparatus of claim 3, wherein the rectifier is an absolute value function.

5. The apparatus of claim 1, wherein the first fully connected layer includes 50 artificial neurons.

6. The apparatus of claim 5, wherein the second fully connected layer comprises 10 artificial neurons.

7. The apparatus of claim 6, wherein first fully connected layer and second fully connected layer apply a transfer function.

8. The apparatus of claim 7, wherein the transfer function is the tansig(x) function.

9. The apparatus of claim 1, wherein first fully connected layer and second fully connected layer apply a transfer function.

10. The apparatus of claim 9, wherein the transfer function is the tansig(x) function.

11. The apparatus of claim 10, wherein the first fully connected layer and the second fully connected layer are developed by training via stochastic gradient descent to produce a set of deep features.

12. The apparatus of claim 1, wherein the first fully connected layer and the second fully connected layer are developed by training via stochastic gradient descent to produce a set of deep features.

13. A method of predicting that a patient is about to exit from a patient support apparatus that is in the field of view of a camera, the method comprising receiving signals representative of images from the camera, capturing time sequenced video images from the camera, inputting the time sequenced video images to a convolution layer and convolving the time sequenced video images with a convolution kernel to produce a defined number of feature maps, inputting the feature maps into a context-aware pooling layer to extract relevant features of interest from the feature maps and generate feature vectors, wherein the context-aware pooling layer applies a rectification factor to the feature vectors to correct for the differences between the developed kernel and the appropriate kernel to be applied to account for a difference in the relationship of the position and orientation of the bed in the developed kernel and the actual position and orientation of the patient support apparatus, inputting a feature vector to a first fully connected layer such that each element of the feature vector is connected to a plurality of artificial neurons in the first fully connected layer and each combination outputs a first connected layer value, inputting the values derived by each combination of first fully connected layer into a second fully connected layer such that each value is connected to a plurality of artificial neurons in the second fully connected layer such that each combination outputs a second connected layer value, inputting the second connected layer values into an output layer which provides a non-exit probability which defines the likelihood that a patient exit event will not occur in a predetermined time and an exit probability which defines the likelihood that a patient exit event will occur in the predetermined time, utilizing the non-exit probability and exit probability to determine the likelihood of a patient exit event to generate a signal when the determined likelihood of a patient exit event exceeds a threshold value, and if the signal is generated based on the determined likelihood of a patient exit event exceeds a threshold value, generating a notification of the impending event.

14. The method of claim 13, wherein the convolution layer applies a rectifier function when the feature maps are generated.

15. The method of claim 14, wherein the rectifier function introduces non-saturating linearity to the features maps.

16. The method of claim 15, wherein the rectifier function is an absolute value function.

17. The method of claim 16, wherein the first fully connected layer includes 50 artificial neurons.

18. The method of claim 17, wherein the second fully connected layer comprises 10 artificial neurons.

19. The method of claim 13, wherein first fully connected layer and second fully connected layer apply a transfer function.

20. The method of claim 19, wherein the transfer function is the tansig(x) function.

21. The method of claim 20, wherein the first fully connected layer and the second fully connected layer are developed by training via stochastic gradient descent to produce a set of deep features.

22. The method of claim 13, wherein the first fully connected layer and the second fully connected layer are developed by training via stochastic gradient descent to produce a set of deep features.

23. The method of claim 13, wherein the first fully connected layer includes 50 artificial neurons.

24. The method of claim 23, wherein the second fully connected layer comprises 10 artificial neurons.

* * * * *